United States Patent [19]

Callne

[11] Patent Number: 5,506,095
[45] Date of Patent: Apr. 9, 1996

[54] DENTAL CAST TRAY SUBASSEMBLY

[75] Inventor: Lars E. Callne, Los Gatos, Calif.

[73] Assignee: Nu-Logic Dental Mfg., Inc., Lyons, Ill.

[21] Appl. No.: 329,372

[22] Filed: Jul. 5, 1994

Related U.S. Application Data

[63] Continuation of Ser. No. 80,066, Jun. 17, 1993, abandoned.

[51] Int. Cl.[6] ............................. A61C 19/00; A61C 11/00
[52] U.S. Cl. ................................. 433/34; 433/60
[58] Field of Search .......................... 433/49, 60, 34, 433/74, 35, 36

[56] References Cited

U.S. PATENT DOCUMENTS

| | | | |
|---|---|---|---|
| 3,436,827 | 4/1969 | Dew | 433/34 |
| 3,702,027 | 11/1972 | Marshall et al. | |
| 3,808,689 | 5/1974 | Spinella | 32/32 |
| 3,838,187 | 11/1974 | Thomas | |
| 4,319,875 | 3/1982 | Beckwith | 433/60 |
| 4,439,151 | 3/1984 | Whelan | 433/60 |
| 4,708,648 | 11/1987 | Weissman | 433/34 X |
| 4,957,435 | 9/1990 | Jinoian et al. | 433/34 |
| 5,076,786 | 12/1991 | Callne | 433/65 |
| 5,129,822 | 7/1992 | Dobbs | 433/34 |
| 5,197,874 | 3/1993 | Silva et al. | 433/74 |
| 5,221,203 | 6/1993 | Callne | |
| 5,306,145 | 4/1994 | Michael | |

FOREIGN PATENT DOCUMENTS 169548  7/1986  United Kingdom.

Primary Examiner—Nicholas D. Lucchesi
Attorney, Agent, or Firm—McDermott, Will & Emery

[57] ABSTRACT

A dental cast tray subassembly for forming a dental cast model and for mounting to a dental articulator. The tray subassembly forms a channel shaped in a configuration of a human jaw to receive a mold material for forming a dental cast model. The channel further includes ribs for registering the model relative to the channel and a release mechanism for releasing the model from the channel. Further included is a platform for interconnecting with connectors for connecting the subassembly to an articulator.

19 Claims, 3 Drawing Sheets

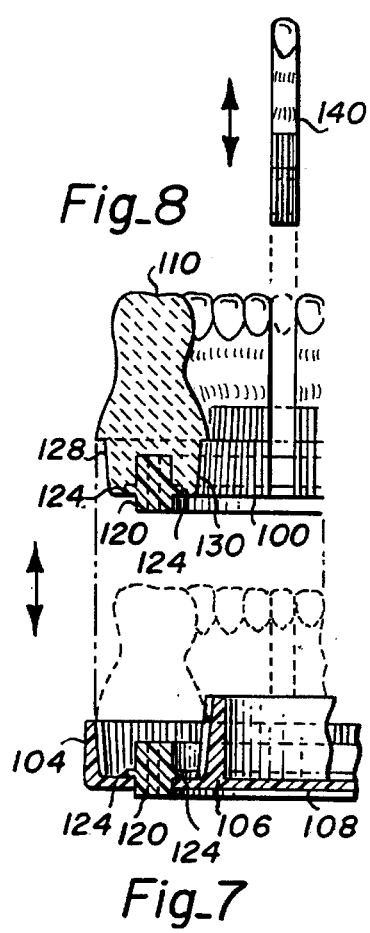
Fig_8
Fig_7
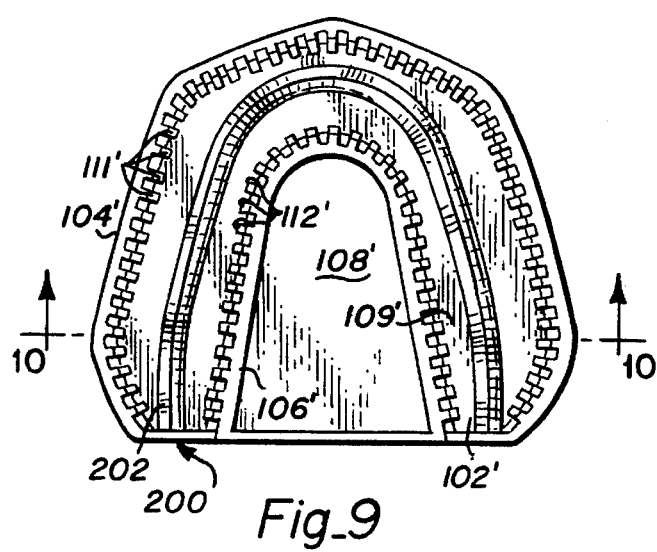
Fig_9
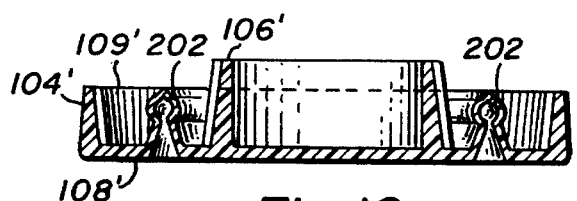
Fig_10
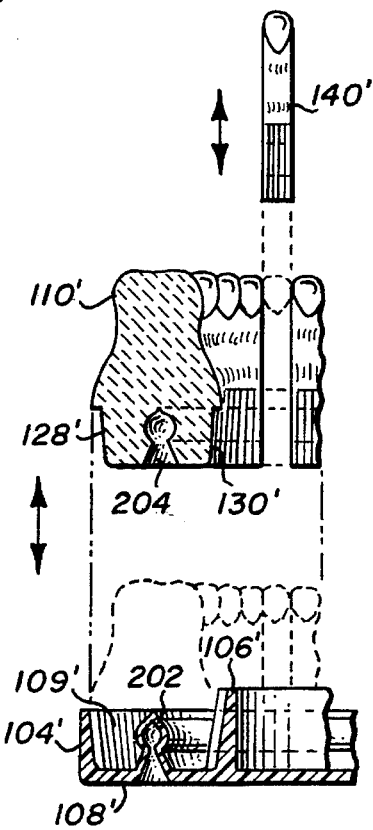
Fig_12
Fig_11

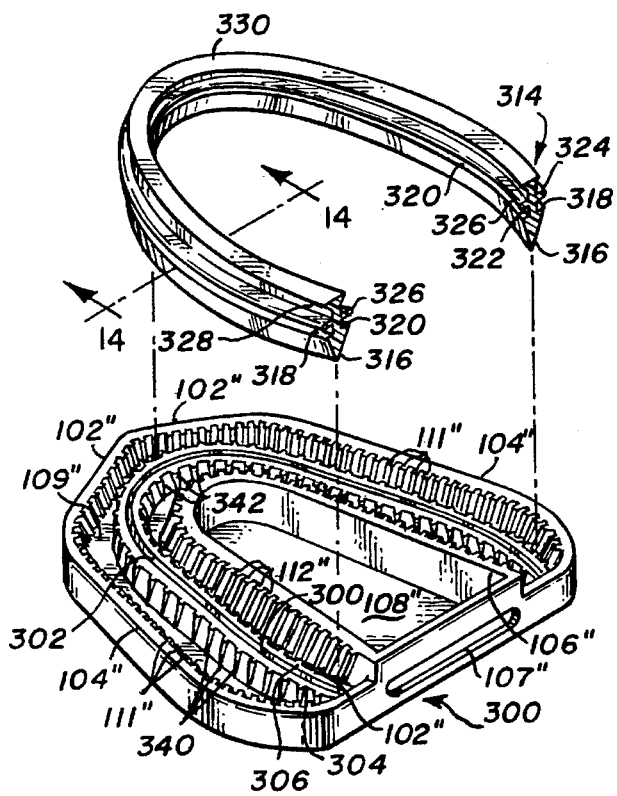
Fig_13
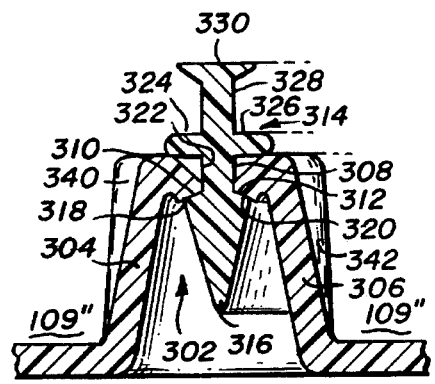
Fig_14
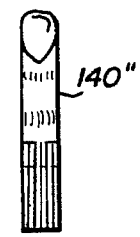
Fig_16
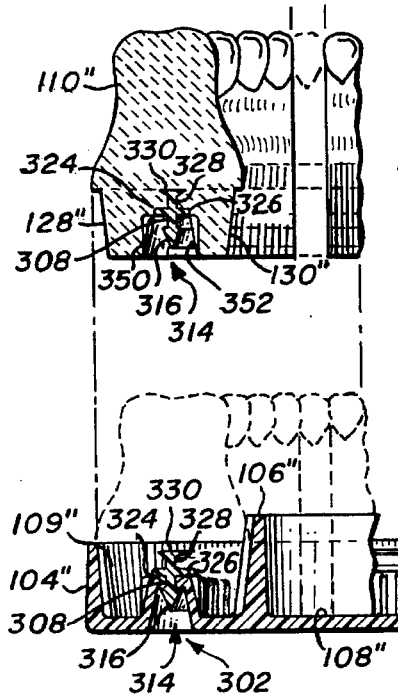
Fig_15

DENTAL CAST TRAY SUBASSEMBLY

This application is a continuation of Ser. No. 08/080,066, filed Jun. 17, 1993 now abandoned.

BACKGROUND OF THE INVENTION

1. Field of the Invention

This invention relates generally to a dental apparatus for assisting dentists and technicians working with dental models for constructing prosthetic denture elements outside the patient's mouth. More particularly, this invention relates to an improved subassembly for interfacing with an articulator so as to provide for dental casts which may be readily assembled to and disassembled from an articulator with proper alignment of an upper dental cast to a lower dental cast and at the same time, provide for the repeated removal and replacement of the dental models from a tray assembly.

2. Description of the Prior Art

With articulators used for supporting impressions of human jaws with artificial teeth and including a lower jaw model and an upper jaw model, it is important that they be capable of simulating the full range of occlusal and masticatory registrations among the patient population. As such, the lower jaw model and the upper jaw model are supported by the articulator to be positioned in a contiguous relationship to provide centric, lateral and protrusive movement relative to each other. This is for simulating a patient's bite. While there are a wide variety of shapes, sizes and arrangements of human jaws and teeth, configurations and occlusion patterns have a broad range among different patients. Nevertheless, the process of making jaw impressions for the fabrication of partial dentures, fix bridges and crowns by using jaw models in a dental laboratory requires that a precise registration and desired occlusal alignment be maintained. Therefore, it is necessary to have articulators that meet these requirements.

Articulators which provide such a wide range of registration and simplicity in use are disclosed in U.S. Pat. No. 5,076,786 entitled "Cast Dental Articulator System and Method", issued on Dec. 31, 1991 to Lars E. Callne. Likewise, another articulator which is further improved is disclosed in U.S. Pat. application Ser. No. 07/863,196, filed Apr. 3, 1992 for "Cast Dental Model Articulator" by Lars E. Callne.

Additionally, to further facilitate and simplify the procedures, there is a need for providing a subassembly wherein the models may be formed and then readily mountable to these articulators. Further, in providing any dentures, bridges, and/or crowns, the costs are of constant concern and it is desirable to provide subassemblies and processes for making such subassemblies which are economical and which lend themselves to be easily usable by technicians.

SUMMARY OF THE PRESENT INVENTION

It is therefore an object of the present invention to provide a dental cast tray subassembly for mounting to a dental articulator which is of simplified structure.

It is a further object of the present invention to provide a dental cast tray subassembly for mounting to an articulator which allows for repeated removal and replacement of the dental model to the articulator.

It is a further object of the present invention to provide a dental model tray subassembly for mounting to an articulator and which provides for repeated removal and replacement of the model from and to the tray and replacement of the tray to the articulator with proper alignment.

Briefly, in a preferred embodiment, the present invention comprises a tray which forms a jaw-shaped canal for receiving a quantity of mold material for forming a dental cast model. Within the tray there is a release means engaged with the tray and for integral molding with the mold material such that the dental cast model can be readily removed from and replaced to the tray. Furthermore, the subassembly includes a registration means within the canal such that the model may be repeatedly removed and replaced within the canal with proper alignment.

An advantage of the present invention is that it further provides a dental cast tray subassembly which can be readily mounted to and removed from an articulator and while also providing for repeated removal and replacement of the model from the tray assembly.

A further advantage of the present invention is that it provides a dental cast tray subassembly which is economical to manufacture.

Another advantage of the present invention is that it provides a dental cast tray subassembly which is readily interfaceable with an articulator and thus easy to use by a technician.

These and other objects and advantages of the present invention will no doubt become obvious to those of ordinary skill in the art after having read the following detailed description of the preferred embodiments which are illustrated in the various drawing figures.

BRIEF DESCRIPTION OF THE DRAWINGS

FIG. 7 is a cross-sectional view of a segment of the tray assembly of FIGS. 1 and 2 with the tray, spinal column and partial dental cast (shown in broken lines) in position;

FIG. 8 is a cross-sectional view of a segment of a spinal column mounted to the partial dental cast removed from the tray of FIG. 7 and with a segmented section of the cast removed;

FIG. 9 is a top perspective view of an alternative tray subassembly of the present invention;

FIG. 10 is a cross-sectional view of the tray subassembly of FIG. 9 taken along the line 10—10;

FIG. 11 is a cross-sectional view of a segment of the tray subassembly of FIG. 9 mounted to a partial dental cast (shown in broken lines) in position;

FIG. 12 is a cross-sectional view of a segment of the partial dental cast removed from the tray subassembly of FIG. 11 and with a segment of the cast removed;

FIG. 13 is a perspective, exploded view of another alternative tray subassembly of the present invention;

FIG. 14 is a cross-sectional view of the tray subassembly of FIG. 13 taken along the line 14—14;

FIG. 15 is a cross-sectional view of a segment of the tray subassembly of FIG. 13 mounted to a partial dental cast (shown in broken lines) in position; and FIG. 16 is a cross-sectional view of a segment of the partial dental cast removed from the tray subassembly of FIG. 15 and with a segment of the cast removed.

DETAILED DESCRIPTION OF THE PREFERRED EMBODIMENT

Figure 1:
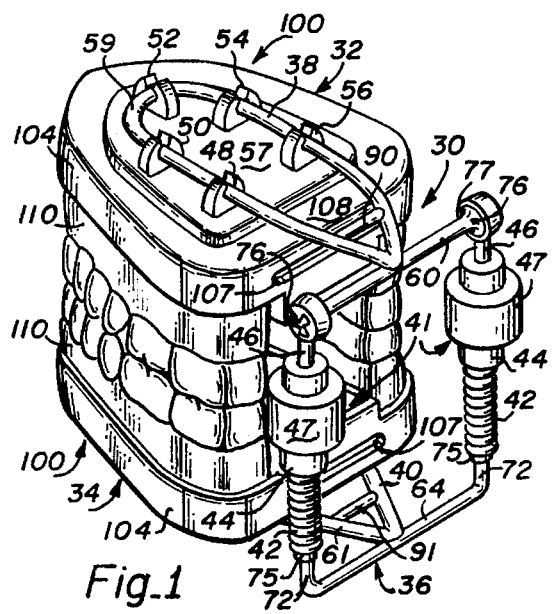
FIG. 1 is a perspective view of an upper and lower dental cast tray subassembly of the present invention, mounted on a dental articulator.

FIG. 1 shows an exemplary articulator system, referred to by the general reference numeral 30 wherein an upper dental cast assembly 32 and a lower dental cast assembly 34 are supported by an articulator 36. The articulator 36 is further depicted and described in U.S. patent application Ser. No. 07/863,196, filed Apr. 3, 1992 for a "Cast Dental Model Articulator" and now U.S. Pat. No. 5,221,203. As illustrated in FIG. 1, the articulator 36 comprises an upper frame member subassembly 38, a lower frame member subassembly 40, and a pair of vertical subassemblies 41. Each subassembly 41 includes a spring coil 42, a threaded, hollow, slip joint frame 44, a dowel 46 and a threaded nut 47. A plurality of clips 48, 50, 52, 54 and 56 mounted on a flat platform 57, secure the upper dental cast 32 to the upper frame member subassembly 38. Though not shown, the lower dental cast 34 is secured to the lower frame member subassembly 40 in a similar manner.

The upper frame member subassembly 38 comprises an upper mounting frame 59 forming a closed loop extending forward from the mid portion of a hinge bar 60. The lower frame member subassembly 40 comprises a lower mounting frame 61 forming a closed loop extending forward from the middle portion of a cross bar 64.

The upper frame member subassembly 38 and the lower frame member subassembly 40 are interconnected through the vertical subassemblies 41. A cross bar 64 is U-shaped with both ends projecting upwardly to form two joint bars 72 each with a threaded end and a collar stop 75 securely threaded to the bottom end of the coil springs 42. The other end of the springs 42 are each connected to the threaded slip joints 44, each of which in turn receives one end of the dowels 46 and the nut 47. Assembled, the nut 47 locks one end of each of the dowels 46 securely within the top of the portion of slip joints 44. The other end of each of the dowels 46 has a bowl-shaped socket hinge receptacle. Each end of the hinge bar 60 comprises a spherical ball-shaped hinge means engaged to one of the hinge receptacles to form a ball-and-socket relationship such that the hinge bar 60 may be rotated and revolved within the hinge receptacle. Thus, the upper frame member subassembly 38 can pivot and rotate about the dowels 46. To provide additional structural strength, a pair of enforcement bars 90 and 91 are included with the frames 59 and 61, respectively.

The upper frame member subassembly 38, the lower frame member subassembly 40, the dowels 46 and platforms 57 may all be composed of plastic materials. The elevation of each of the dowels 46 may be independently adjusted depending on its position within its associated slip joint 44. Each end of the hinge bar 60 is in the form of a ball 76 fitted within a socket 77 at the end of the dowels 46. Thus, each end of the hinge bar 60 may be at an independent elevation as a result of the ball-and-socket arrangement of the socket-shaped hinge receptacle hinge means. The articulator 36 provides for convenient adjustments in X, Y and Z ordinate planes of the subassembly 38 relative to the subassembly 40 such that accurate simulations of the occlusal registration can be accomplished. Additionally, due to the flexibility of its structure, the upper frame member subassembly 38 with its hinge means can be removed from and re-installed in the hinge receptacles merely by hand manipulations and without requiring prior removal of the dowels 46 from the slip joints 44. Thus, the operational procedures in assembling and disassembling the articulator 36 to support the cast dental models can be performed with or without the dental cast subassemblies 32 and 34 in place and without any tools.

The upper dental cast assembly 32 and the lower dental cast assembly 34 each include a dental cast tray subassembly, referred to by the general reference character 100 and depicted in further detail in FIGS. 2–5. The tray subassembly 100 includes a tray 102 having an outer peripheral sidewall 104 formed in the shape of a jaw and an inner peripheral sidewall 106, likewise formed in the shape of a jaw. A slot 107 is formed in the rear side of the sidewall 104. A bottom wall 108 is integral with and interconnects the sidewalls 104 and 106. As such, the walls 104, 106 and 108 establish a convex canal 109 of a jaw shape to receive a quantity of mold material for forming a die stone dental cast model 110 as illustrated by the dental cast assemblies 32 and 34 in FIG. 1, and comprised of a mold material formed from a dental impression of a patient. The slot 107 provides for accommodation of other types of articulators having other means for mounting.

The tray 102 also includes a registration means in the form of a plurality of ribs 111 formed within the sidewall 104 and a plurality of ribs 112 integral with the inner peripheral sidewall 106.

Figure 2:
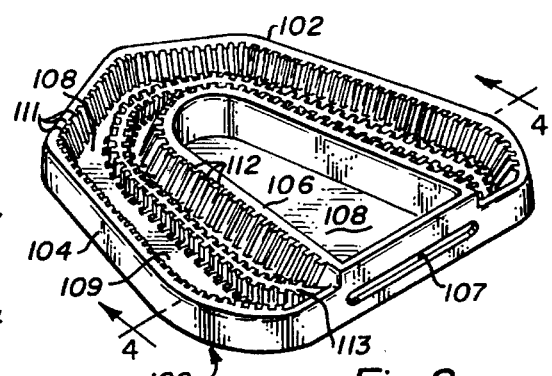
FIG. 2 is a perspective view of the tray subassembly shown in FIG. 1.
Figure 4:
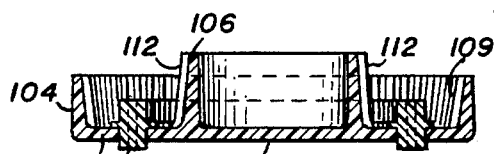
FIG. 4 is a cross-sectional view of the tray of FIG. 2 and taken along the line 4—4.
Figure 3:
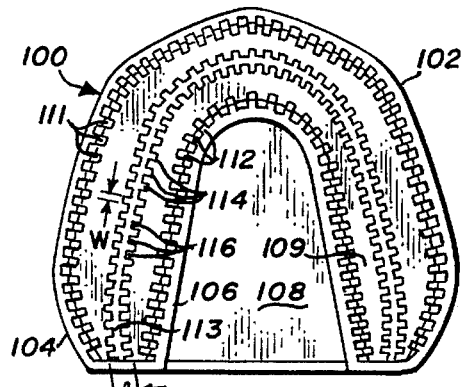
FIG. 3 is a top view of the tray subassembly of FIGS. 1 and 2 without the spinal column.
Figure 5:
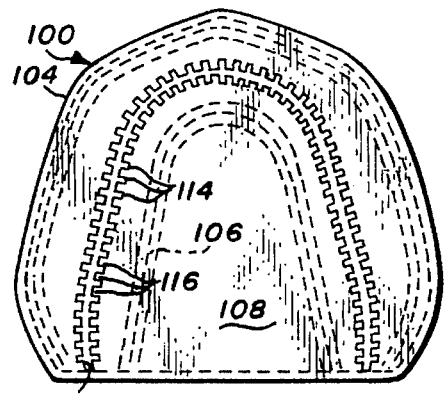
FIG. 5 is a bottom view of the tray of FIG. 2.
Figure 6A:
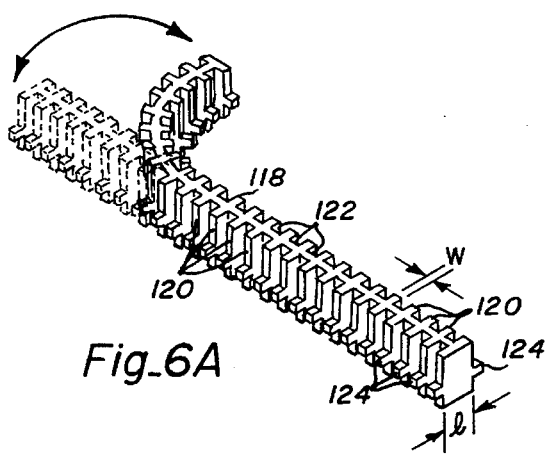
FIG. 6A is a perspective top view of the spinal column of the tray assembly of FIGS. 1 and 2.
Figures 6B, 6C:
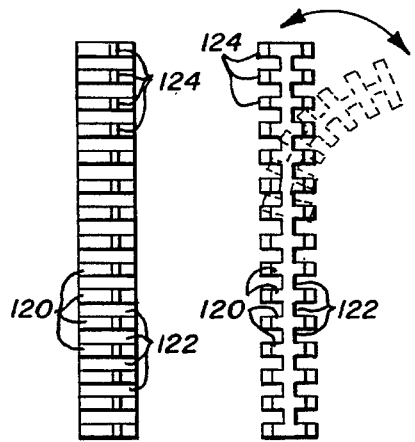
FIG. 6B is a side view of the spinal column of FIG. 6A.
FIG. 6C is a top view of the spinal column of FIG. 6A.

Likewise, the dental cast tray subassembly 100 further includes a release means including an elongated slot 113 extending along the entire length of the bottom wall 108 within the canal 109. The slot 113 includes a plurality of rectangular laterally extending openings 114 of length "l" and width "w". Each of the openings 114 is interconnected with a rectangular longitudinal opening 116. An elongated spinal column 118 with a string of keys 120 aligned and interconnected by a spinal cord member 122. Each of the keys 120 has a lateral dimension of "l" and width "w" which fits within the lateral openings 114. Likewise, each key 120 also includes a pair of studs 124. As reflected in FIGS. 6A–6c, the spinal column 118 is configured so as to be flexible along the spinal cord 122. As illustrated in FIGS. 2–4 the spinal column 118 fits within the slot 113 and is supported within the canal 109 with the studs 124 abutting the interior of the bottom wall 108 with the lower portion of the keys 120 in the openings 114. Thus, with the spinal column 118 in place the model cast material may be poured within the canal 109. Then the dental impression is placed over said material to form the dental cast model 110.

The materials for the tray 102 and spinal column 118 are selected of a plastic material which will adhere to and conform with the material of the dental cast model 110. Such material is poured within the channel 109 formed within the tray 100 with the elongated spinal column 118 in place. Then, after the material is imprinted with the denture impression to reproduce the model of a patient's teeth and jaw, and after said material cures, it is adherent to and integral with the spinal column 118 as reflected in FIG. 7. Then, pressure may be applied to the bottom surface of the keys 120 of the spinal column 118 such that the dental cast may be released from the tray 102 with the integral spinal column 118 as depicted in FIG. 8. As it is released, the ribs 110 and 111 have formed registration grooves 128 about the outer periphery of the models and registration grooves 130 about the internal periphery of the model as reflected in FIG. 8. Thus, after the dental cast model is removed from the tray 102, it may be segmented as desired. For example, where the imprint shows the teeth to be replaced or otherwise serviced, that section of the model can be separated away, as reflected by a segment 140 in FIG. 8. Then, a replacement partial denture, crown, bridge or the like may be built and replaced in the area vacated by the segment 140. Next, the entire model may be replaced into the tray 102 and due to the registration grooves, alignment is assured within the tray 102. Next, the entire tray 102 may be mounted onto the articulator frame member subassemblies 38 and 40. This can be done by the platform 57 being adhered to the planar surface of the bottom wall 108 and clips 48, 50, 52, 54 and 56 secured to the frame 59. As such, the entire dental cast subassemblies 32 and 34 can be readily removable to and from an articulator system. Likewise, the individual dental cast models 110 can be readily removed and reinserted within the tray 102 with assurance of repeated proper alignment. Thus, there is always assurance of proper registration due to the registration means in the form of the ribs 111 and 112 and the spinal column 118. Also, the entire tray 102 with the ribs 111 and 112 may be molded in a unitary piece which provides for economics as well as accuracy. In fact, the tray 102 may be molded with a one-shot injection mold.

Likewise, the release means may take various forms. The release means in the form of the spinal column 118 provides for a unitary member which may also be manufactured in an injection molding process. Likewise, the spinal column 118 may be molded with a one-shot mold. In selecting the materials for the spinal column 118, since it will become a permanent adhesion to the model material, it may be selected to have more permanent adhesion to the model material than is necessary for that of the tray 102 since the ribs 111 and 112 will not be making permanent adherence to such materials. However, this will be a choice of the manufacturer.

FIGS. 9–12 reflect an alternative embodiment of the present invention and illustrates a dental cast tray subassembly referred to by the general reference character 200. Those elements in the embodiment 200 common to those of the tray assembly embodiment 100 carry the same reference numeral distinguished by a prime designation. The primary distinction between the tray embodiment 200 and the tray subassembly embodiment 100 is the release means. The tray subassembly 200 includes an elongated key-shaped spring member 202 which extends along the entire length of the bottom wall 108' within the canal 109'. Thus, as the dental cast material is poured into the canal 109', it forms around the elongated spring member 202. After the dental cast material cures, due to the pliancy of the spring member 202, the cured dental cast model 110' may be removed from the canal 109'. This leaves a complimentary key-shaped channel 204 in the model. Thus, after the model 110' is removed, it may be severed or otherwise dealt with as reflected in FIG. 12. Then, when it is necessary to replace the partial and secure it back in place within the canal 109', the model will be registered within the tray 102' due to the ribs 111' and 112' with the registrations 128' and 130' and due to the pliancy of the spring member 202. The nature of the materials of the spring member 202 may be of the same material as that of the tray 102'.

FIGS. 13–16 reflect another alternative embodiment of the present invention and illustrates a dental cast tray subassembly referred to by the general reference character 300. Those elements in the embodiment 300 common to those of the embodiment 100 carry the same reference numeral distinguished by a double prime designation. The primary distinction between the embodiment 300 and the embodiments 100 and 200 is the release means. The tray subassembly 300 includes an elongated key-shaped segrated spring member 302 which extends along the entire length of the bottom wall 108" within the canal 109". The spring member 302 includes two legs 304 and 306 separated by a spacing 308. The spacing 308 is formed in an inverted V-shape to form a pair of stress points 310 and 312 at the spacing 308. A spline 314 fits within the spacing 308. The spline 314 includes a tapered projection 316 with a pair of lips 318 and 320 which interface with the stress points 310 and 312. Above the lips 318 and 320 the spline 314 has a shank 322 with two lateral lips 324 and 326 to interface with a top edge of the legs 304 and 306. Above the lips 324 and 326 is a vertical projectionf 328 with a ledge 330 at its ends. Thus, the spline 314 extends along the length of the spring member 302 in the spacing 308 with the lips 318 and 320 engaged at the points 310 and 312. The legs 304 and 306 act as springs such that the spacing 308 may be urged wider as the projectoin 316 is mounted or removed and then springs into place about the lips 318 and 320 to hold the spline in place.

Within the exterior of the legs 304 and 306 are a plurality of of ribs 340 along the longitudinal length of the leg 304 and a plurality of ribs 342 along the longitudinal length of the leg 306. Therefore, with the subassembly 300 registration ribs are within the exterior surface of the dental model to interface with the ribs 111" and 112". Also, internal registration ribs interface with the ribs 340 and 342.

Thus, with the spline 314 in place, as the dental cast material is poured into the canal 109", it forms around the elongated spring member 302 and the spline 314. After the material cures, due to the pliancy of the legs 304 and 306 of the spring member 302, the cured dental cast model may be removed from the canal 109" with the spline 314 embodied in the material. This leaves a complimentary interior groove in the model to interface with the ribs 340 and 342 and exterior grooves to interface with the ribs 111" and 112". Thus, after the model is removed, it may be severed or otherwise dealt with as reflected in FIG. 16. Then, when it is necessary to replace the dental partial model 140" and secure it back in place within the canal 109", the model 140" will be registered within the tray 102" due to the ribs 111" and 112" with the registrations 128" and 130", and the ribs 340 and 342 with registrations 350 and 352, and due to the pliancy of the spring member 302. The nature of the materials of the spline 314 may be of the same material as that of the tray 102" or another type of material. With the spacing formed by the projection 328 and ledge 330, it forms a further lock on the identical partial model material.

Although the present invention is described in terms of the presently preferred embodiments, it is to be understood that such disclosure is not to be interpreted as limiting. Various alterations and modifications will no doubt become apparent to those skilled in the art after reading the above disclosure. Accordingly, it is intended that the appended claims be interpreted as cover all alterations and modifications as fall within the true spirit and scope of the invention.

I claim:

1. A dental cast tray subassembly for forming a dental cast model and for mounting to a dental articulator, the subassembly comprising:

a tray with an outer jaw-shaped periphery with a pair of sidewalls integral with a bottom wall to form a convex canal for receiving a quantity of mold material for forming a dental cast model;

release means engaged within the tray and about said bottom wall to interface with and adhere to said mold material to release a cured dental cast model from the tray, the release means comprising an elongated continuous slot along said bottom wall with a series of laterally projecting contiguous openings aligned along the length of said continuous slot and an elongated continuous spinal column of a length coinciding with the length of said slot and further comprising a string of interconnected keys with each key projecting laterally and configured of a shape to fit within and interface with one of said contiguous openings; and registration means within at least one of said sidewalls and about an interior periphery of said canal to interface with said mold material and to register a position of a cured dental cast model.

2. The dental cast tray subassembly of claim 1 wherein, the registration means includes a plurality of ribs integral with and spaced apart about the interior periphery of said canal to form corresponding slots within a sidewall of said cured dental cast model.

3. The dental cast tray subassembly of claim 1 wherein, the registration means includes a plurality of ribs within each of said sidewalls.

4. The dental cast tray subassembly of claim 1 wherein, the tray includes a tray platform for interconnecting to a frame of a dental articulator.

5. The dental cast tray subassembly of claim 4 wherein, said tray platform includes a planar surface interconnected with attachment means for attachment to clips for securing the tray platform to a dental articulator.

6. The dental cast tray subassembly of claim 1 wherein, each of said string of keys is shaped to include a portion projecting within said canal and a portion interlocking with said slot.

7. The dental cast tray subassembly of claim 6 wherein, each of said string of keys further includes a portion for resisting lateral movement of said portion of said string of keys interlocking with said slot.

8. The dental cast tray subassembly of claim 6 wherein, the registration means includes a plurality of ribs integral with and spaced apart about the interior periphery of said canal to form corresponding slots within a sidewall of said cured dental cast model.

9. The dental cast tray subassembly of claim 8 wherein, the registration means includes a plurality of ribs within each of said sidewalls.

10. The dental cast tray subassembly of claim 1 wherein, each of said keys project from said bottom wall to within said canal such that when a mold material is placed within said canal it adheres to said keys of said spinal column; whereby a cured dental cast may be removed from the tray upon application of pressure to said keys from beneath said openings for overcoming adherance of said spinal column and said bottom wall.

11. The dental cast tray subassembly of claim 10 wherein, the registration means includes a plurality of ribs integral with and spaced apart about the interior periphery of said canal to form corresponding slots within a sidewall of said cured dental cast model.

12. The dental cast tray subassembly of claim 11 wherein, the registration means includes a plurality of ribs within each of said sidewalls.

13. The dental cast tray subassembly of claim 1 wherein, the registration means includes a plurality of ribs integral with and spaced apart about the interior periphery of said canal to form corresponding slots within a sidewall of said cured dental cast model.

14. The dental cast tray subassembly of claim 13 wherein, the registration means includes a plurality of ribs within each of said sidewalls.

15. A dental cast tray subassembly for forming a dental cast model and for mounting to a dental articulator, the subassembly comprising:

a tray with an outer jaw-shaped periphery with a pair of sidewalls integral with a bottom wall to form a convex canal for receiving a quantity of mold material for forming a dental cast model;

release means engaged within the tray and about said bottom wall to interface with and adhere to said mold material to release a cured dental cast model from the tray, the release means comprising an elongated spring member including a pair of pliant legs formed as one with the tray and positioned within said canal and separated by a spacing, a spline with a first projection for inserting within said spacing and a second projection for projecting above said spacing to interface with said mold material; and registration means within at least one of said sidewalls and about an interior periphery of said canal to interface with said mold material and to register a position of a cured dental cast model.

16. The dental cast tray subassembly of claim 15 wherein, said legs include a plurality of ribs integral with and spaced apart about the exterior periphery of each leg to form correspondinbg internal slots within said cured dental cast model.

17. The dental cast tray subassembly of claim 16 wherein, the registration means further includes a plurality of ribs integral with and spaced apart about the interior periphery of said canal to form corresponding slots within a sidewall of said cured dental cast model.

18. The dental cast tray subassembly of claim 17 wherein the registration means includes a plurality of ribs within each of said sidewalls.

19. The dental cast tray subassembly of claim 18 wherein, said spline includes a lip for interengaging with a stress point of said spring member to position and secure said spline in place within said spacing.

* * * * *